United States Patent [19]

Kammerer

[11] Patent Number: 4,974,114
[45] Date of Patent: Nov. 27, 1990

[54] ENERGY RECOVERY CIRCUIT FOR ELECTROTHERAPY DEVICE

[75] Inventor: Gilbert E. Kammerer, Del Mar, Calif.

[73] Assignee: LTI Biomedical, Inc., San Diego, Calif.

[21] Appl. No.: 309,162

[22] Filed: Feb. 13, 1989

[51] Int. Cl.$^5$ .............................................. A61N 1/00
[52] U.S. Cl. ......................................... 361/159; 600/9
[58] Field of Search ..................... 128/419 F, 419 PG; 361/159; 600/9, 11, 12, 13

[56] References Cited

U.S. PATENT DOCUMENTS

| | | | |
|---|---|---|---|
| 3,717,153 | 2/1973 | Bowers | 128/419 PG |
| 3,893,462 | 7/1985 | Manning | 128/421 |
| 4,266,532 | 5/1981 | Ryaby et al. | 128/1.5 |
| 4,574,809 | 3/1986 | Talish et al. | 128/419 F |
| 4,654,574 | 3/1987 | Thaler | 320/14 |
| 4,665,920 | 5/1987 | Campbell | 128/419 F |

OTHER PUBLICATIONS

Bedford et al., *Principles of Inverter Circuits*, pp. 48–54, 184–195, (John Riley, NY: 1964).
Dixon, "The Effects of Leakage Inductance on Switching Power Performance", p. 2–1, Unitrode Corporation, Massachusetts, 1983.
Haver, "A Designer's Guide to Switching Power Supplies (Part 1)", *Power Conversion Int'l.*, pp. 47–48, (Jul./Aug. 1981).
Lilienstein, "A New Overbiased Transformer Converter Combines Current-Source and Mag Amp Control Characteristics", Proc. 10th Natl., *solid-State Power Conversion Conf.* (POWERCON 10), vol. B-3, p. 2, 1983.
McMurray et al., "A Silicon-Controlled Rectifier Inverter with Improved Commutation", *AIEE Trans.*, vol. 80, Part 1, pp. 531–542, (Nov., 1961).
Spadaro, "Bioelectric Stimulation of Bone Formation: Methods, Models and Mechanisms", *J. Bioelectricity*, vol. 1, No. 1, pp. 99–128 (1982).

*Primary Examiner*—Francis Jaworski
*Assistant Examiner*—George Manuel
*Attorney, Agent, or Firm*—Brown, Martin, Haller & McClain

[57] ABSTRACT

An energy recovery system for an electrotherapy device, particularly for bone healing, which permits the device to be small, light and portable, and to have extended battery life. Included are a drive voltage source and a ground reference potential. Driving transistors are between an inductive load and, relatively, the voltage source and ground potential, with a storage capacitor connected between the latter two. The voltage source is commonly a battery, preferably a zinc-air battery. Induction load power is applied when both transistors turn on simultaneously. For energy recovery, diodes are connected between the first terminal of the inductive load and the ground potential and between the second terminal of the inductive load and the high voltage source, such that they are reversed biased when the drive transistors are conducting. When drive power is removed from the inductive load by switching off the drive transistors, a reverse EMF is established in the inductive load. As the inductive load magnetic field collapses, a reverse voltage is developed across the inductor higher than the applied voltage by an amount sufficient to forward bias the diodes. Thus, current flows from the inductive load through the diodes to the storage capacitor. Recovery of the energy stored in the inductor continues until the energy remaining is insufficient to maintain current flow to the storage capacitor.

9 Claims, 6 Drawing Sheets

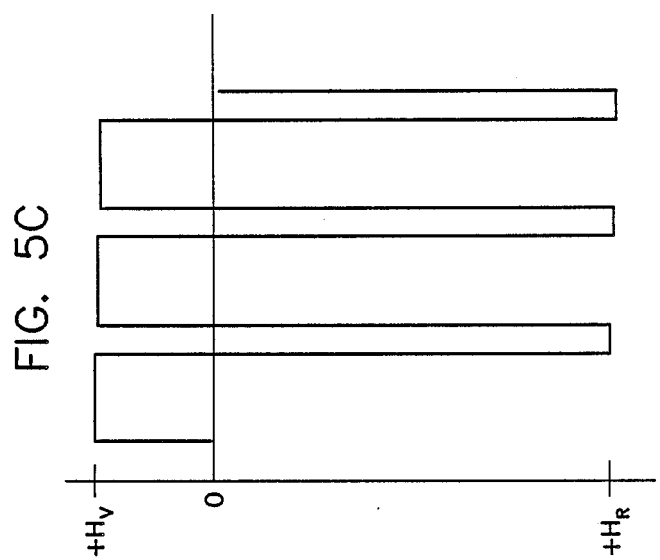
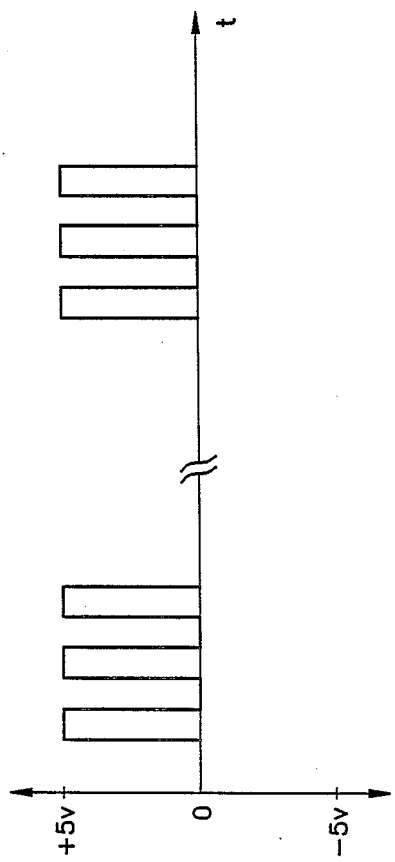
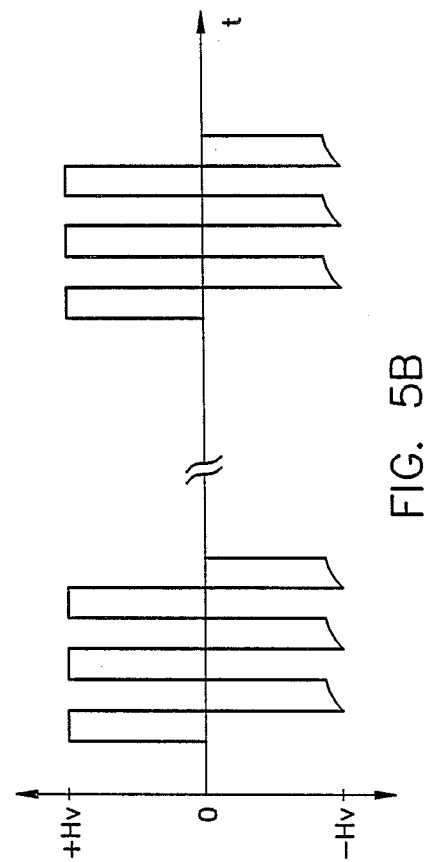
FIG. 5A
FIG. 5B
FIG. 5C

ENERGY RECOVERY CIRCUIT FOR ELECTROTHERAPY DEVICE

FIELD OF THE INVENTION

The present invention relates to the field of electromagnetic medical therapy ("electrotherapy") systems. More specifically, it relates to electrotherapy systems intended to promote healing of bone fractures.

BACKGROUND OF THE INVENTION

The use of electric or electromagnetic fields to promote healing, particularly the healing of fractured bones, has been investigated since the early 19th century. See Spadaro, "Bioelectric Stimulation of Bone Formation: Methods, Models and Mechanisms," *J.Bioelectricity*, 1, 1, 99-128 (1982). In early research, direct current techniques were used by applying electrodes to the skin or via the use of implanted electrodes into the bone. More recently, research has focused on mechanisms which encourage growth through the use of electromagnetic fields to induce voltage and current effects within the tissue. These techniques have been particularly useful in treating non-healing or "non-union" fractures by inducing healing of bones which do not readily heal naturally.

An example of a technique for the use of electromagnetic radiation to promote bone growth is illustrated in U.S. Pat. No. 4,266,532 to Ryaby et al. This patent shows an effective technique for promoting bone growth. However, the technique disclosed by Ryaby et al. requires the use of power supplied from a standard wall socket. Electrotherapy is only useful as long as the patient uses it. Being tethered to the wall is a sufficient annoyance such that many patients will not follow the electrotherapy regimen prescribed by their doctors. Therefore, it is desirable to provide an electromagnetic therapy system which is completely portable.

The apparatus illustrated in U.S. Pat. No. 4,574,809 to Talish et al. is a portable electrotherapy system. The Talish et al. system includes a mounting structure which allows the user to recharge the batteries in the therapy device by connecting the device to a base section which contains recharging circuitry. However, because of the small size of the housing for batteries in such a device, and because of the high energy requirements of electrotherapy, the batteries of the Talish et al. device must be recharged often. This also is often of sufficient inconvenience to many patients to cause noncompliance with the required therapy regimen.

It is impractical to try to provide for extended battery life by enlarging the size of the battery, since that merely enlarges the size of the electrotherapy device which the patient wears and increases its weight and thus effectively defeats the portability feature, since many patients will simply not use a device which is bulky, heavy or inconvenient to wear or carry.

The most effective way of making a battery-powered electrotherapy device sufficiently small and light that it is easily portable and yet be therapeutically effective in practice is to enhance the service life of the battery. This permits the patient to get prolonged treatment without having to change or recharge the device's battery. Maintaining the small size in combination with the enhanced battery life makes the device much more acceptable to patients, and consequently they will be more willing to wear or use the device for the prescribed treatment period.

One method of enhancing battery lifetime while yet retaining the desirable small battery size is to recover the energy stored in the electromagnetic transducer of the electrotherapy system. Generally, the transducers used in electrotherapy to produce the electromagnetic radiation are highly inductive. Because a great deal of the energy applied to these inductive transducers is stored in the transducers in the form of magnetic energy, it would be desirable to recover that energy and direct it back to the control circuitry of the electrotherapy system for reuse. One possible system to recover such energy is shown in U.S. Pat. No. 4,654,574 to Thaler. The elaborate method shown in Thaler involves the use of ancillary energy recovery coils which are inductively coupled to the transducer coil. During the collapse of the magnetic field induced by the inductor, an electromotive force (EMF) is generated in the energy recovery coil which is then applied to a storage capacitor. However, energy recovery in the Thaler system is limited by the coupling between the transducer coil and the energy recovery coil and by losses in the energy recovery coils.

It would therefore be of substantial value to have an electrotherapy device which is sufficiently small and light to be portable, and in which battery life is sufficiently long that users do not find frequency of battery replacement to be of concern.

SUMMARY OF THE INVENTION

The invention herein is an energy recovery system for an electrotherapy device which includes an inductive load, and permits the device to be physically small, portable and have good battery life. In its broadest form, the system comprises:

a storage capacitor having a first plate connected to a source of positive potential and a second plate connected to a reference potential;

first switching means having a first current handling terminal connected to said positive potential, a second current handling terminal connected to a first terminal of said inductive load and having a control terminal;

second switching means having a first current handling terminal connected to said reference potential, a second current handling terminal connected to a second terminal of said inductive load and having a control terminal;

control means connected to said control terminals of said first and second switching means;

a first diode having a cathode lead connected to said first terminal of said inductive load and an anode terminal connected to said second plate of said storage capacitor; and a second diode having a cathode lead connected to said first plate of said storage capacitor and an anode connected to said second terminal of said inductive load.

Preferably the first and second switching means are field effect transistors and the control means are driving circuits connected to astable clock circuitry for producing a particular signal which has proven effective in electrotherapy regimens.

In an embodiment for use with a non-symmetric signal, the circuit further comprises the second diode having a cathode lead connected to a first plate of a second storage capacitor which is maintained at a positive potential greater than the positive potential applied to the first storage capacitor, a second plate of the second storage capacitor being connected to the reference potential, and means for transferring energy from the second storage capacitor to the first storage capacitor.

By use of the present invention, over 90% of the energy induced in the inductive transducer may be recovered and stored in the storage capacitor for use with the next charging cycle of the transducer. This high efficiency allows for extremely long battery lifetimes and promotes proper therapy by reducing the burden on the patient with respect to use and maintenance of the device and its batteries. For example, in one embodiment of the present invention, a battery pack may be mounted in a belt mounting system. Using the highly efficient circuitry of the present invention, the batteries used may last for several weeks. If rechargeable batteries are used to power the device, then while one battery pack is in use, a second battery pack may be connected to a charging device so that the maintenance required to be performed by the patient can be limited to periodically changing the battery packs over a course of weeks rather than every few hours as required with prior art devices.

While the present invention is useful with all types of batteries, it finds particularly beneficial use with zincair, manganese dioxide, silver oxide and related batteries.

BRIEF DESCRIPTION OF THE DRAWINGS

FIG. 5A is a time graph of the signal provided by power control 2 to transducer 3;

FIG. 5B is a time graph showing the actual signal generated across transducer 3;

FIG. 5C is a time graph of an asymmetric signal which can be used in this invention.

DETAILED DESCRIPTION AND PREFERRED EMBODIMENTS

The invention herein is an energy recovery system for an electrotherapy device which allows the device to be light weight, small and portable. All of these properties are of importance if the device is to find practical acceptance in medical therapy. It is well known that therapy patients are lax in following prescribed therapy regimens when the devices they are required to use are heavy, bulky or keep them confined to a single location or position during each therapy session. It goes without saying that if a therapy device is not regularly used, the intended healing will not be accomplished or will require an unduly extended period.

A common failing of prior art devices was in their inability to optimize use of the electrical or electromagnetic energy produced by the device. In particular, the devices usually did not permit recovery of energy. This is of critical significance for battery-powered devices, since in such systems where energy could not be recovered and redirected to the battery, the battery would discharge quickly and frequent battery replacement or recharging was required. Commonly battery life was measured in hours. With the energy recovery system of this invention, battery life is extended to several weeks, rather than a few hours. In many cases this frees the patient entirely from having to be concerned about battery replacement, since the service life is on the order of the frequency of the patient's visits to the physician or therapist, and the latter can replace the battery as part of the patient's regular treatment.

Even in those few cases (such as described in the Thaler patent (supra.) where provision was made for energy recovery, the recovery means contemplated were bulky and heavy, so that the overall device was much less acceptable to the patient.

Figure 1:
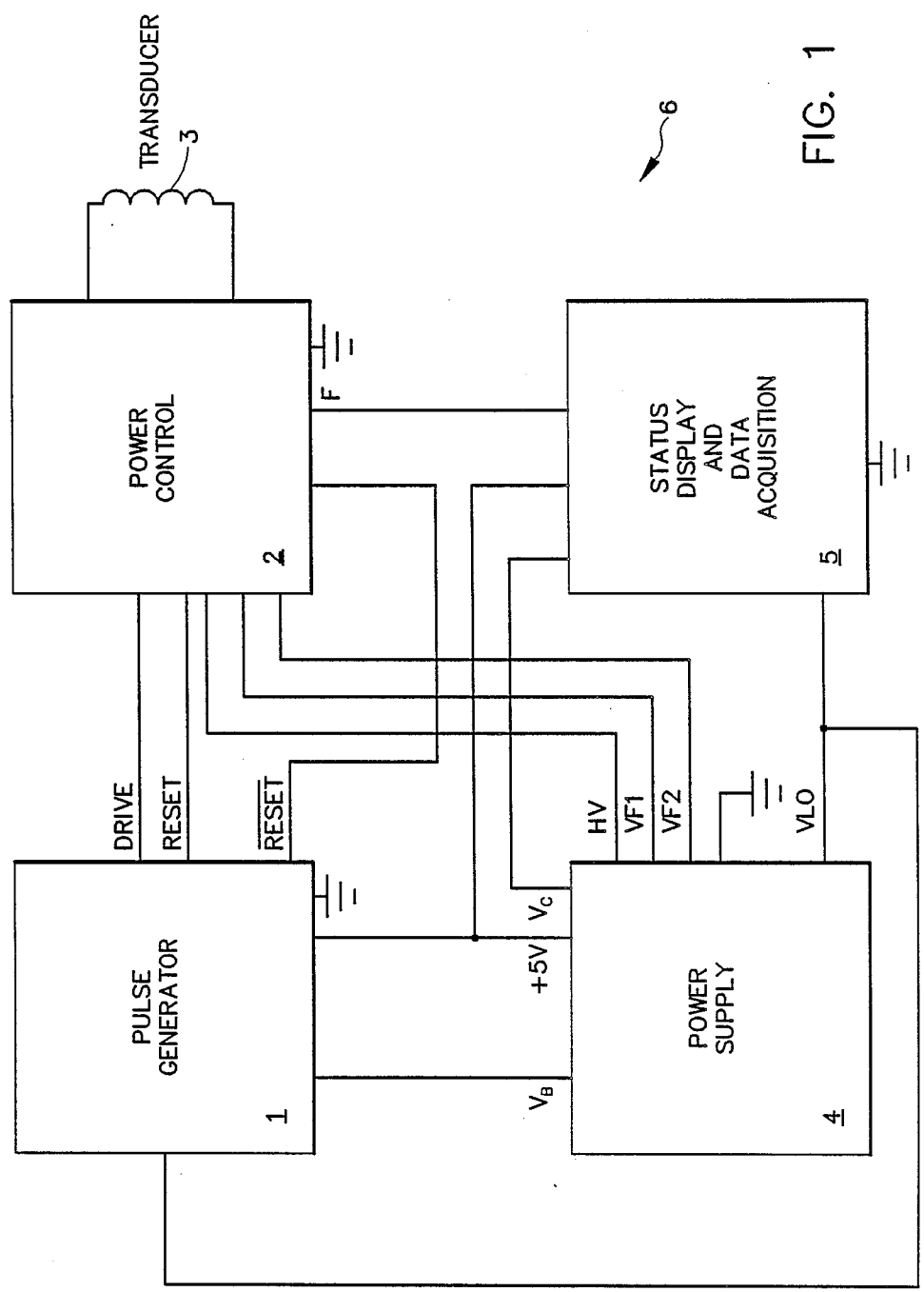
FIG. 1 is a block diagram showing the interrelationship of the circuit components in one embodiment of the present invention.

The invention herein can be best understood by reference to the drawings. FIG. 1 is a block diagram showing the interconnection between functional components in one embodiment of the present invention. Pulse generator 1 generates a series of bursted pulses in a manner known to be effective for inducing the desired therapeutic healing. Pulse generator 1 provides the appropriate train of bursted pulses and drive to power control unit 2. Pulse generator 1 also generates a reset signal for the quiescent portions of the signal provided by pulse generator 1 on line DRIVE. Power control unit 2 drives transducer 3 in response to the signal provided on line DRIVE. Power control unit 2 receives reference voltages HV, VF1 and VF2 from power supply 4. Power control unit 2 uses the HV (high voltage) to drive transducer 3.

Power supply 4 provides normal battery operating voltage $V_B$, an accurate +5 volts and a $V_C$ voltage which is backed by an auxiliary battery. Power supply unit 4 also provides an adjustable high voltage power source up to 40 volts on line HV, a power supply VF1 which is approximately 12 volts below the level provided on lead HV and a power supply VF2 which is approximately 12 volts above ground.

Status display and acquisition unit 5 monitors the operation of circuit 6 by providing visual displays, audio warnings and stored data relating to the operation of electrotherapy circuit 6. The circuitry used in unit 5 will be conventional circuitry such as counters, registers and display drivers configured to process signals F, V and VLO to log the actual treatment hours in a form readable by the attending physician or therapist. Conventional circuits in this section also provide visual and audible indication of the need for battery replacement or of system faults such as broken or shorted transducer leads. The particular circuitry selected will not be critical to the operation of the energy recovery system of this invention.

Figure 2:
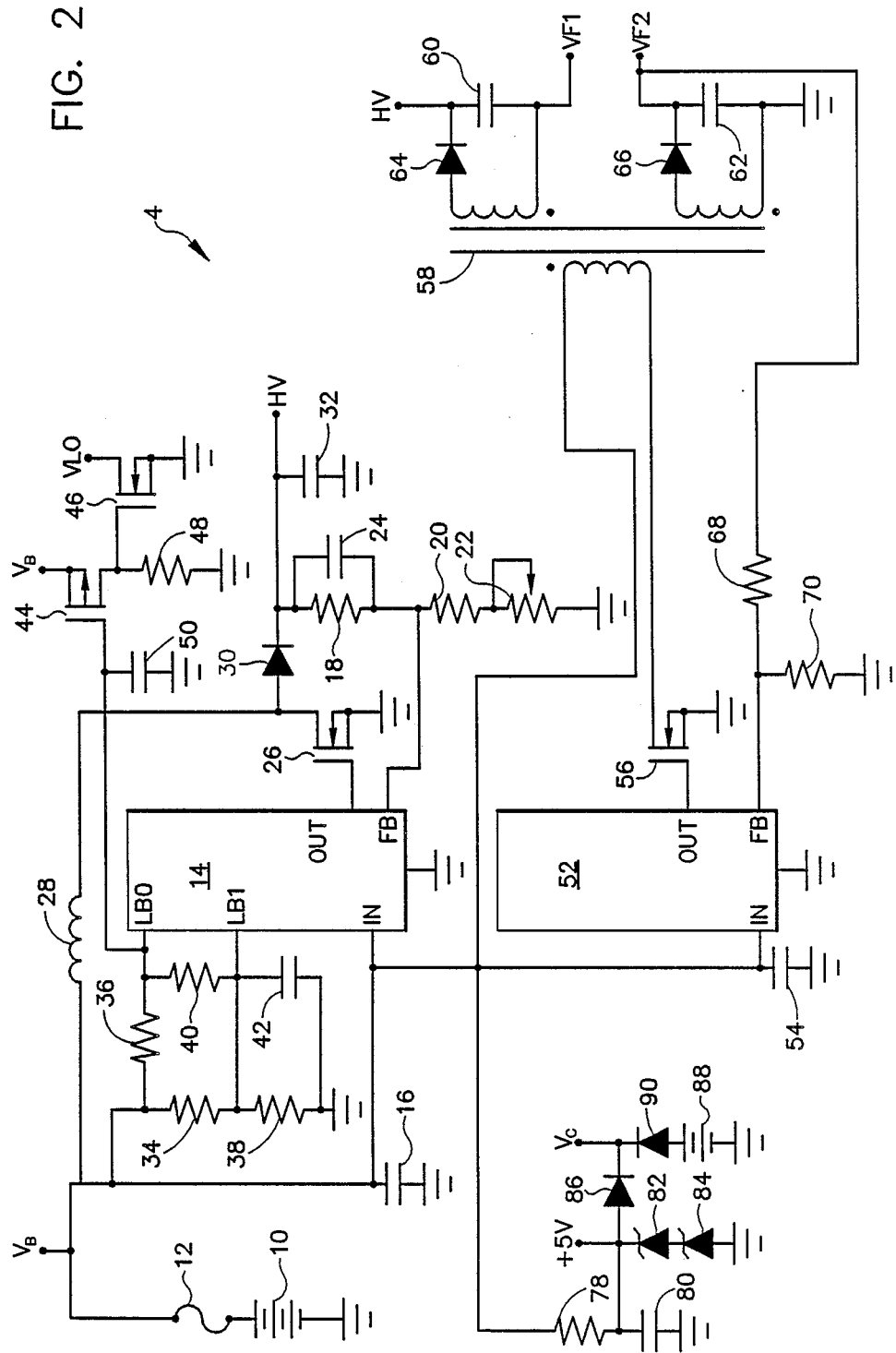
FIG. 2 is a schematic diagram of power supply 4 of FIG. 1.

FIG. 2 is a schematic diagram showing the operation of power supply 4. The main source of power for power supply 4 is battery pack 10. Battery pack 10 consists of batteries which may be rechargeable or non-rechargeable types according to patient procedure, battery pack size and weight considerations, and economy. While any type of battery may be used to advantage with the circuitry of this invention, it is particularly preferred to use it with batteries of types such as zinc-air, manganese dioxide and silver oxide, since those are the most advantageous for long term stable and consistent power production in an electrotherapy device. Potential damage to battery pack 10 is minimized by fuse 12 which will blow in the event that there is a short from $V_B$ to ground. Those devices which may operate directly on unregulated battery supply are connected to $V_B$.

The high voltage for driving the transducer is generated by switching integrated circuit 14 and its associated circuitry. Integrated circuit 14 can be any one of many current switching voltage regulators such as the Maxim 643. Integrated circuit 14 is supplied with $V_B$ level voltage after first being smoothed by capacitor 16. Integrated circuit 14 operates by monitoring the level on the FB input pin. The voltage level on the FB input pin is established by the voltage divider network comprising resistors 18, 20 and 22. Resistor 22 is a rheostat to provide a variable voltage level on output terminal HV. Capacitor 24 helps condition the signal provided to input pin FB of integrated circuit 14. When the signal provided on the OUT pin of integrated circuit 14 causes transistor 26 to turn on, a current is generated through inductor 28 from $V_B$ to ground. When the signal on pin OUT goes to a low voltage, transistor 26 turns off and the magnetic field flowing through inductor 28 causes a reversed voltage drop, thereby generating a higher voltage level than $V_B$ at HV through diode 30. Capacitor 32 smoothes out the pumping effect of the switching system to provide a relatively smooth voltage level 1 at output terminal HV.

Integrated circuit 14 includes internal circuitry for determining when a low battery level is occurring. Resistors 34, 36, 38 and 40 and capacitor 42 are connected to pins LBO and LBI. These components serve to generate a low voltage output signal provided to the gate of transistor 44. When a low voltage is provided to the gate of transistor 44, a high voltage is provided to the gate of transistor 46 which causes a low voltage to be provided at output terminal VLO. Resistor 48 provides a load for transistor 44 and capacitor 50 prevents a spurious signal at the gate of transistor 44 from causing an erroneous VLO output signal.

Integrated circuit 52 can also be a Maxim 643. $V_B$ is provided to input IN as with integrated circuit 14 and capacitor 54 smoothes the signal provided to input IN as does capacitor 16 for integrated circuit 14. Transistor 56 is turned on and off by the signal provided on pin OUT which draws current through transformer 58. The current through the primary coil of transformer 58 causes energy to be stored in the magnetic core of transformer 58. The secondary windings of transformer 58 are connected such that diodes 64 and 66 are reversed biased during the time that transistor 56 is turned on. When transistor 56 is turned off by pin OUT the stored energy causes a reverse voltage to be generated on primary and secondary coils of transformer 58. Diodes 64 and 66 are then forward biased and the stored energy is transferred to capacitor 60 and 62. As explained below, the power supplies VF1 and VF2 are important in the circuitry which provides the high voltage output drive for the transducer. A voltage divider provided by resistors 68 and 70 provides feedback to integrated circuit 52 which acts to maintain VF2 constant. VF1 tracks VF2 by virtue of the close coupling of the secondary windings of transformer 58 and nearly equal current drain required from VF1 and VF2. Certain components in pulse generator circuit 1 and status display circuit 5 (FIG. 1) require highly regulated 5-volt voltage supply. This is provided by resistor 78 and zener diodes 82 and 84. In normal operation, the 5 volt supply is provided to output terminal $V_C$ through diode 86, thus providing an output voltage of about 4.3 volts. $V_C$ is the voltage terminal which is maintained at a constant voltage level by back-up battery 88 through diode 90. When battery 10 is fully charged and in place, battery 88 does not provide any power to terminal $V_C$. However, when battery 10 is removed or underpowered, battery 88 maintains terminal $V_C$ at a voltage level of 3.0 volts to support or maintain memory of the current treatment time, so that the doctor can determine exactly how long the electrotherapy system has been in use.

Figure 3:
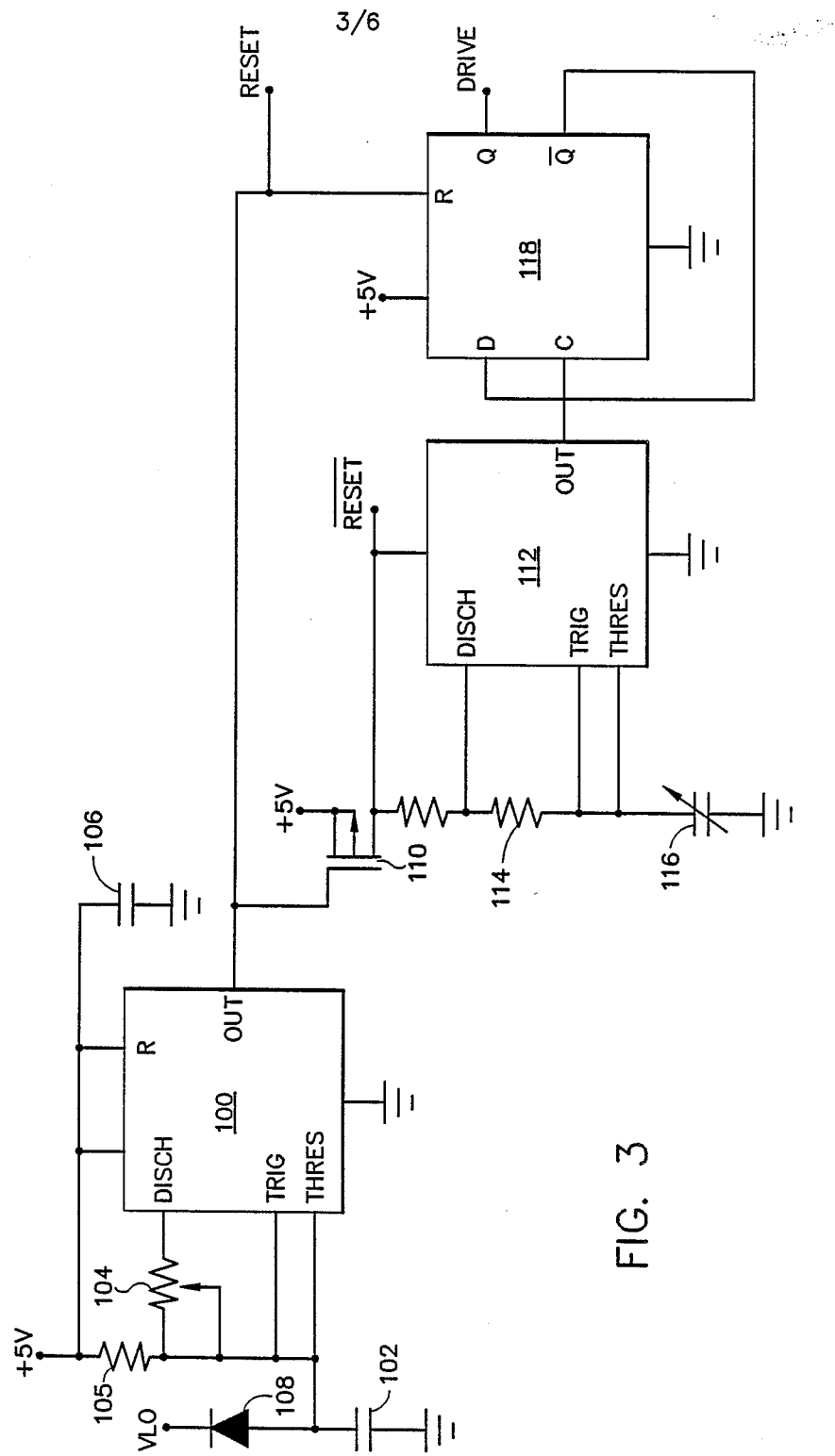
FIG. 3 is a schematic diagram of pulse generator 1 of FIG. 1.

FIG. 3 is a schematic diagram showing the operation of pulse generator 1 of FIG. 1. Integrated circuit 100 is a clock circuit such as a standard 551 clock circuit. The clock rate and output duty cycle of integrated circuit 100 is set by the values of capacitor 102 and resistors 104 and 105. Capacitor 106 prevents spurious pulses from causing a reset signal to integrated circuit 100. Clock circuit 100 will continue to provide an output signal having a set frequency of 15 HZ until a VLO signal is provided on input terminal VLO which causes integrated circuit 100 to stop operating. The output signal of integrated circuit 100 is provided to the gate of transistor 110 which operates clock circuit 112.

Integrated circuit 112 is also a clock circuit such as a 551 integrated circuit. The clock rate of integrated circuit 112 is set to a much higher rate than integrated circuit 100 by resistors 114 and 115 and variable capacitor 116. The output cf integrated circuit 112 is provided to the clock input terminal of D flip flop 118. D flip flop provides a signal conditioning function so that the output provided on the DRIVE output terminal is a pure square wave. In addition, D flip flop 118 has the function of dividing by two the frequency of the signal provided on the output pin of integrated circuit 112.

When the output signal of integrated circuit 100 is a high level, no power is supplied to integrated circuit 112 and thus integrated circuits 112 and 118 are in a quiescent state. During this period of time, a high output signal is provided on output terminal RESET which causes the power control circuit 2 (FIG. 1) to force the output signal of power control circuit 2 to a quiescent state. When a low voltage output signal is provided on the pin of integrated circuit 100, transistor 110 conducts and provides a power source for integrated circuit 112 and a drive signal is provided on the Q output pin of flip flop 118. Also, a low voltage signal is provided on output terminal RESET which is provided to power control circuit 2 (FIG. 1).

Figure 4:
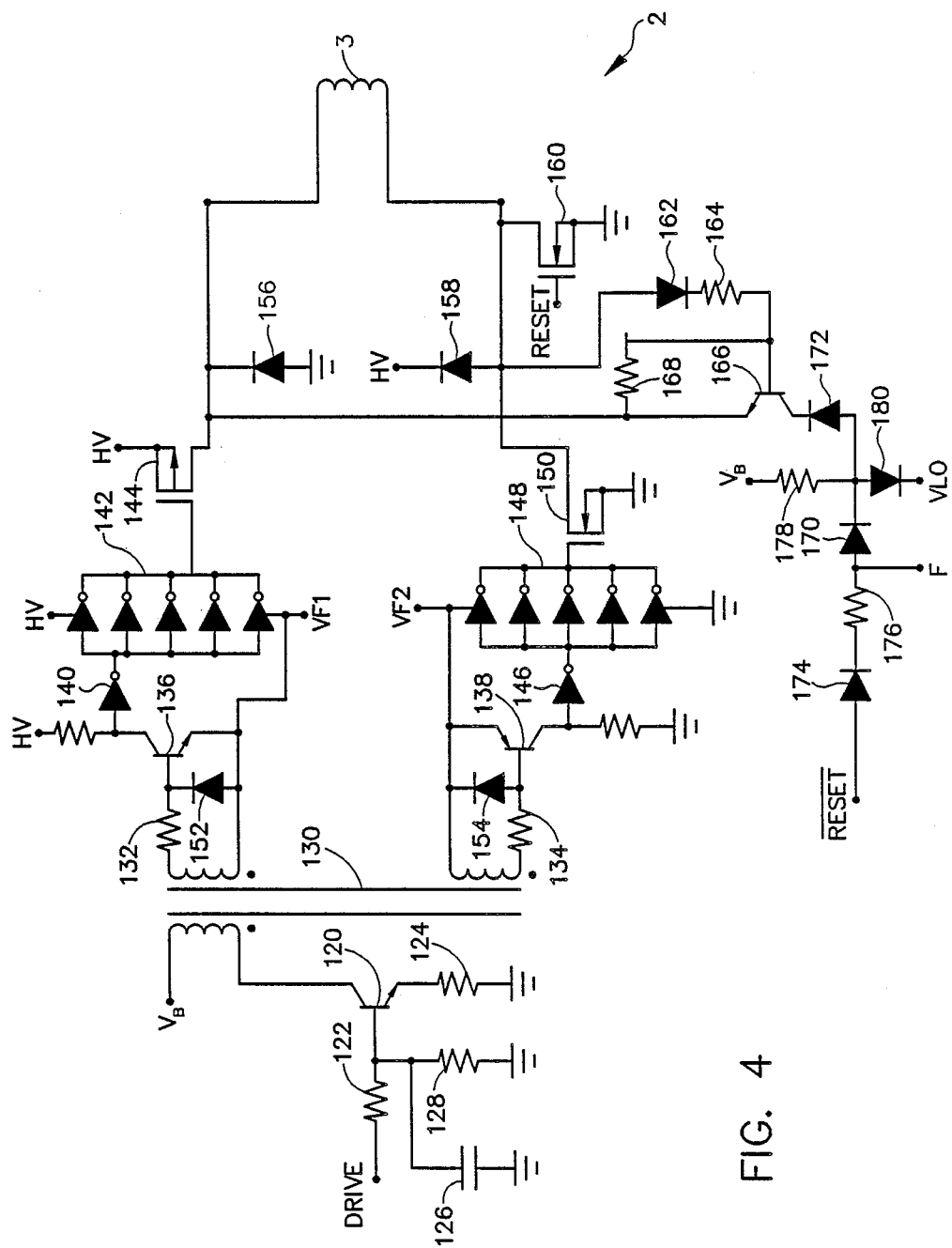
FIG. 4 is a schematic diagram of power control 2 of FIG. 1.

FIG. 4 is a schematic diagram of power control circuit 2 of FIG. 1. The drive signal from pulse generator 1 is provided on input terminal DRIVE to transistor 120 through resistor 122. Capacitor 126 and resistor 128 provide a base to emitter voltage drop for transistor 120. When transistor 120 is conducting through the primary winding of transformer 130, transistor 120 acts as a current source which causes an induced current in the secondary windings of transformer 130, which in turn provides base current to transistors 136 and 138 causing transistors 136 and 138 to conduct. When transistor 136 conducts, a low input signal is provided to inverter 140 which then provides a high input signal to the input terminal of inverter bank 142. This high input signal causes a "low" output signal equivalent to VF1 to be applied to the gate of transistor 144. This low signal applied to the gate of transistor 144 causes transistor 144 to conduct and apply HV to one lead of coil 3. At the same time, when transistor 138 conducts, a "high" voltage signal equivalent to VF2 is provided to the input terminal of inverter 146 which causes a low input signal to be provided on the input terminal of inverter bank 148. The low input signal causes a "high" output signal equivalent to VF2 to be provided to the gate of transistor 150 which connects the other terminal of transducer 3 to ground through transistor 150. Inverter banks 142 and 148 are provided to provide the high drive current necessary to quickly turn on and off power transistors 144 and 150.

When transistor 120 does not conduct, transistors 136 and 138 are off and a high voltage signal is applied to the input terminal of inverter 140 and a low voltage input signal is provided to the input terminal of 146. This causes inverter banks 142 and 148 to turn off transistors 144 and 150. Diodes 152 and 154 ar provided to limit the reverse voltage applied to the base terminals of transistors 136 and 138. When transistors 144 and 150 are not conducting, the current through transducer 3 causes a reverse EMF which causes a negative voltage higher than HV to be provided across transducer 3. This voltage causes diodes 156 and 158 to be forward biased and thus a current flows through to the HV power terminal. This current charges capacitor 32 of FIG. 2 during the off-cycle of transistors 144 and 150 so that a high amount of the energy pumped into transducer 3 is recovered and stored in capacitor 32 of FIG. 2.

FIG. 5A shows the signal provided on input terminal DRIVE. FIG. 5B is a graph showing the voltage drop across transducer 3. As can be seen from FIG. 5B, during the off-cycle of transistors 144 and 150, a high negative voltage occurs across transducer 3 which diminishes over time until either the voltage across transducer 3 is less than the voltage required to forward bias diodes 156 and 158 or transistors 144 and 150 are turned on.

To provide the appropriate therapeutic signal, it is necessary that the residual energy stored in transducer 3 be removed during the quiescent periods of the signal. This is done through transistor 160 which is turned on by the RESET signal indicating a quiescent state.

In order to properly monitor the application of electrotherapy to the patient, the circuit must determine when a proper signal has been applied to transducer 3 and send the appropriate signal to the display system 5 (in the embodiment shown in FIG. 4 the output to unit 5 is designated terminal F). One sure way of determining whether the proper signal has been applied to transducer 3 is to sense whether a reverse EMF is generated by the collapse of the magnetic field through the transducer. This is accomplished in power control circuit 2 through diode 162, resistor 164 and transistor 166. When a reverse EMF is present across transducer 3, diode 162 is forward biased and transistor 166 is turned on by the forward bias of its base emitter junction through the voltage drop generated across resistor 168. When transistor 166 is on, the output terminal F is pulled low through diodes 170, 172 and 156. Thus a low signal is provided on output terminal F. If a fault occurs and proper reverse EMF does not occur, output terminal F is pulled high through the $\overline{\text{RESET}}$ signal provided on the $\overline{\text{RESET}}$ input terminal which pulls the voltage on output terminal F high through diode 174 and resistor 176. Positive voltage and a load are provided to transistor 166 through resistor 178 which is connected to $V_B$. When a low voltage signal is provided due to inadequate power supply, output terminal F is pulled low through diode 180 which is pulled low by the VLO signal.

Figure 6:
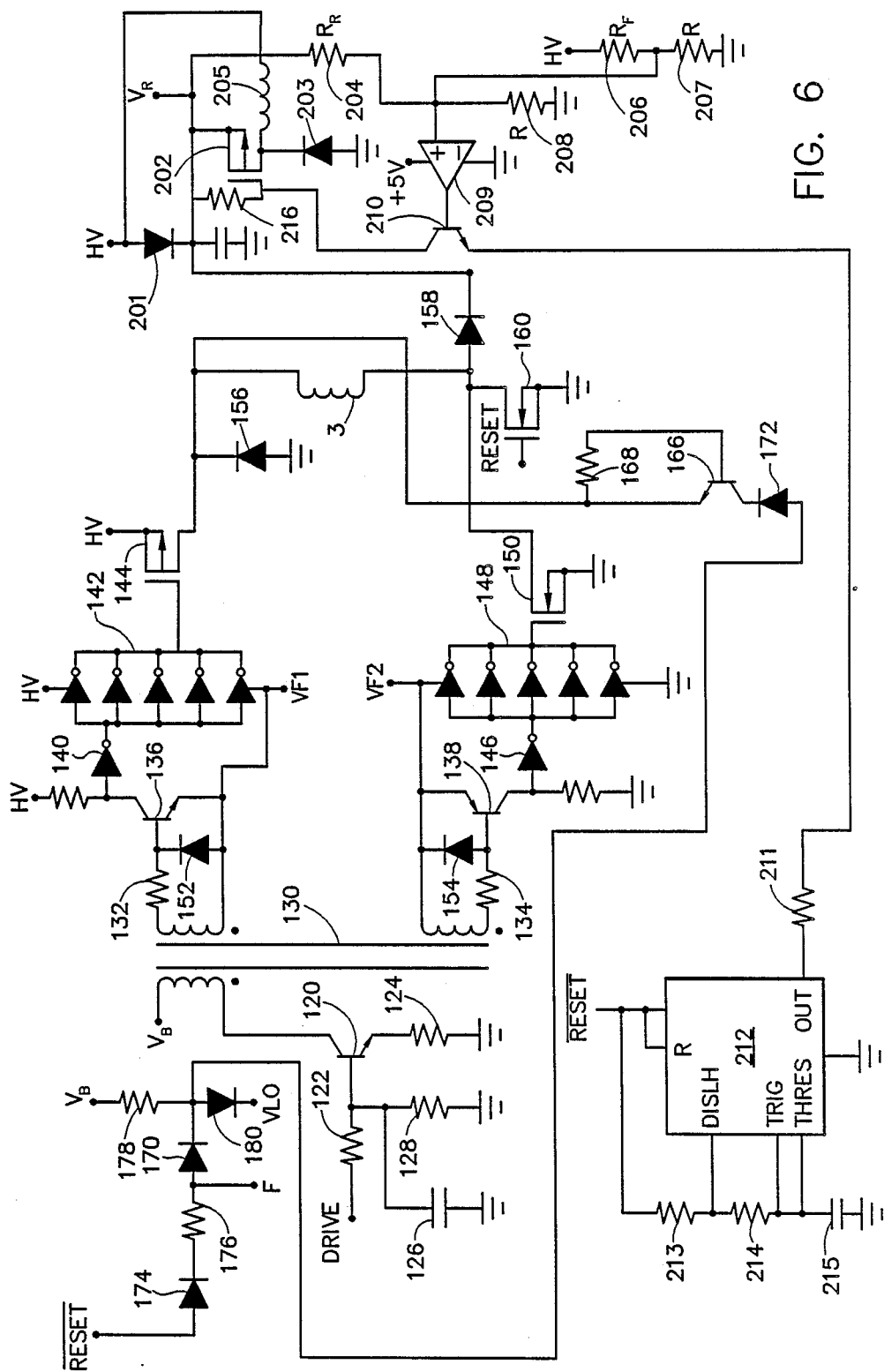
FIG. 6 is a schematic diagram of circuitry which utilizes an asymmetric signal.

The circuit modifications shown in FIG. 6 provide a means of driving load 3 with an asymmetrical signal voltage such as that shown in FIG. 5C. Such a non-symmetrical signal voltage is provided by returning the cathode of diode 158 to the positive plate of capacitor 200 which will be maintained at a voltage ($V_R$) greater than HV. The voltage $V_R$ is maintained constant by the action of components 202, 203 and 205 and control signals as discussed below. The ratio of $V_R$ to HV is determined by resistors 204, 206, 207 and 208 as given by the formulas:

$$V_R/HV = (R+R_R)/(R+R_F)$$

and when $R_R > R_F >> R$, $V_R/HV \approx R_R/R_F$.

Comparator circuit 209 senses the differences between a sampled value of HV and a sampled value of $V_R$. Resistors 206 and 207 provide the sample of HV and resistors 204 and 208 provide the sample of $V_R$. If the sampled value of $V_R$ is greater than the sampled value of HV, then the output of comparator 209 will be positive, providing base current to transistor 210. When the output pulse generator circuit 212 is also at ground potential, transistor 210 will conduct and current will flow through resistor 216. The voltage developed across resistor 216 appears at the gate of transistor 202, causing transistor 202 to conduct. Current will then flow from the positive plate of capacitor 200 through transistor 202 and inductor 205 to the positive plate of capacitor 32 which is connected to terminal HV as shown in FIG. 2.

Diode 203 provides a current path for current flowing in inductor 205 to continue when transistor 202 returns to the non-conducting state. When the sampled value of $V_R$ falls below the sampled value of HV the output of comparator 209 will be low and transistor 210 will not conduct when the output of pulse generator 212 is at ground potential. Resistors 213 and 214, along with capacitor 215, control the frequency and duty cycle of pulse generator circuit 212.

To conserve energy pulse generator circuit 212 only functions when signal $\overline{\text{RESET}}$ is at a high voltage, since it is only during this time that energy is transferred from load 3 to capacitor 200. Diode 201 serves to charge capacitor 200 to voltage HV when power is initially applied to the circuit.

Although a specific embodiment of the invention is herein described, it is not to be construed as limiting the scope of the invention. Many embodiments will become apparent to those skilled in the art in light of the teachings of this specification. For example, many substitutions of different integrated circuits and transistor types fall within the scope of the invention. The scope of the invention is limited only by the claims appended hereto.

I claim:

1. An energy recovery circuit comprising:
   a storage capacitor having a first plate connected to a source of positive potential and the second plate connected to a reference potential;
   first switching means having a first current handling terminal connected to said positive potential, having a second current handling terminal connected to a first terminal of said inductive load and having a control terminal;
   second switching means having a first current handling terminal connected to said reference potential, having a second current handling terminal connected to a second terminal of said inductive load and having a control terminal;

control means connected to said control terminals of said first and second switching means;

a first diode having its cathode lead connected to said first terminal of said inductive load and its anode terminal connected to said second plate of said storage capacitor; and a second diode having its cathode lead connected to said first plate of said storage capacitor and its anode lead connected to said second terminal of said inductive load.

2. A circuit as in claim 1 wherein said inductive load is an electric to electromagnetic transducer.

3. A circuit as in claim 1 wherein said first and second switching means are transistors.

4. A circuit as in claim 1 wherein said control means provides a signal which causes a train of bursted oscillating signals to be provided to a transducer.

5. A circuit as in claim 1 wherein said control means provides a signal which causes a train of continuously oscillating signals to be provided to a transducer.

6. A circuit as in claim 1 wherein said source of positive potential is a battery.

7. A circuit as in claim 6 wherein said battery of is of the zinc-air type, manganese dioxide type or silver oxide type or the like.

8. A circuit as in claim 7 wherein said battery is of the zinc-air type.

9. A circuit as in claim 1 further comprising said second diode having its cathode lead connected to a first plate of a second storage capacitor which is maintained at a positive potential greater than the positive potential applied to the first storage capacitor, the second plate of said second storage capacitor connected to said reference potential, and means for transferring energy from said second storage capacitor to said first storage capacitor.

* * * * *